US008685053B2

(12) United States Patent
Brown et al.

(10) Patent No.: US 8,685,053 B2
(45) Date of Patent: Apr. 1, 2014

(54) TETHER EQUIPPED CATHETER

(75) Inventors: Brian Brown, Hanover, MN (US);
Jason Hill, Cottage Grove, MN (US);
John R. Moberg, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2561 days.

(21) Appl. No.: 10/444,048

(22) Filed: May 22, 2003

(65) Prior Publication Data
US 2004/0236367 A1    Nov. 25, 2004

(51) Int. Cl.
*A61M 29/00*    (2006.01)

(52) U.S. Cl.
USPC ............ 606/194; 604/103.11; 623/1.11

(58) Field of Classification Search
USPC ............ 606/108, 191, 194, 195; 604/103.11, 604/96.01, 913; 623/1.11
See application file for complete search history.

(56) References Cited

U.S. PATENT DOCUMENTS

| | | | |
|---|---|---|---|
| 4,251,305 A | 2/1981 | Becker et al. ............ 156/86 |
| 4,636,272 A | 1/1987 | Riggs ............... 156/158 |
| 4,943,278 A | 7/1990 | Euteneuer et al. ........ 604/96 |
| 4,964,409 A | 10/1990 | Tremulis ............. 128/657 |
| 5,046,497 A | 9/1991 | Millar ............... 128/637 |
| 5,100,381 A | 3/1992 | Burns ................. 604/96 |
| 5,154,725 A | 10/1992 | Leopold ............. 606/194 |
| 5,261,879 A | 11/1993 | Brill ................ 604/96 |
| 5,279,562 A | 1/1994 | Sirhan et al. ............ 604/96 |
| 5,281,203 A | 1/1994 | Ressemann ........... 604/164 |
| 5,295,961 A | 3/1994 | Niederhauser et al. ...... 604/96 |
| 5,304,134 A | 4/1994 | Kraus et al. ............ 604/96 |
| 5,306,247 A | 4/1994 | Pfenninger ............ 604/96 |
| 5,346,505 A | 9/1994 | Leopold ............. 606/194 |
| 5,370,616 A | 12/1994 | Keith et al. ........... 604/102 |
| 5,370,655 A | 12/1994 | Burns ............... 606/194 |
| 5,383,853 A | 1/1995 | Jung et al. ............ 604/96 |
| 5,387,193 A | 2/1995 | Miraki ............... 604/96 |
| 5,395,334 A | 3/1995 | Keith et al. ........... 604/102 |
| 5,397,306 A | 3/1995 | Nobuyoski et al. ........ 604/96 |
| 5,439,447 A | 8/1995 | Miraki ............... 604/96 |
| 5,480,383 A | 1/1996 | Bagaoisan et al. ........ 604/96 |
| 5,490,837 A * | 2/1996 | Blaeser et al. ........ 604/103.11 |
| 5,522,818 A | 6/1996 | Keith et al. ........... 604/102 |
| 5,549,556 A | 8/1996 | Ndondo-Lay et al. ....... 604/102 |
| 5,567,203 A | 10/1996 | Euteneuer et al. ........ 604/96 |
| 5,702,439 A | 12/1997 | Keith et al. ............ 604/96 |
| 5,980,484 A | 11/1999 | Ressemann et al. ....... 604/96 |
| 6,129,708 A | 10/2000 | Enger ............. 604/103.04 |
| 6,273,879 B1 | 8/2001 | Keith et al. ........... 604/523 |
| 6,319,229 B1 | 11/2001 | Kim et al. ............ 604/103 |
| 6,361,529 B1 | 3/2002 | Goodin et al. .......... 605/524 |
| 6,368,302 B1 | 4/2002 | Fitzmaurice et al. ..... 604/103.04 |
| 6,461,347 B1 | 10/2002 | von Hoffmann .......... 604/508 |
| 6,520,951 B1 | 2/2003 | Carrilla, Jr. et al. ....... 604/516 |

* cited by examiner

*Primary Examiner* — Vy Q Bui
(74) *Attorney, Agent, or Firm* — Vidas, Arrett & Steinkraus, P.A.

(57) ABSTRACT

A catheter assembly comprises a manifold positioned at a proximal end of the catheter assembly. A tether member has a proximal end region fixedly engaged to a portion of the manifold. A proximal tubular member has a first end region engaged to the manifold. The proximal tubular member is disposed about at least a portion of the tether member. At least a portion of the tether member distal of the manifold is fixedly engaged to at least a portion of the proximal tubular member.

20 Claims, 2 Drawing Sheets

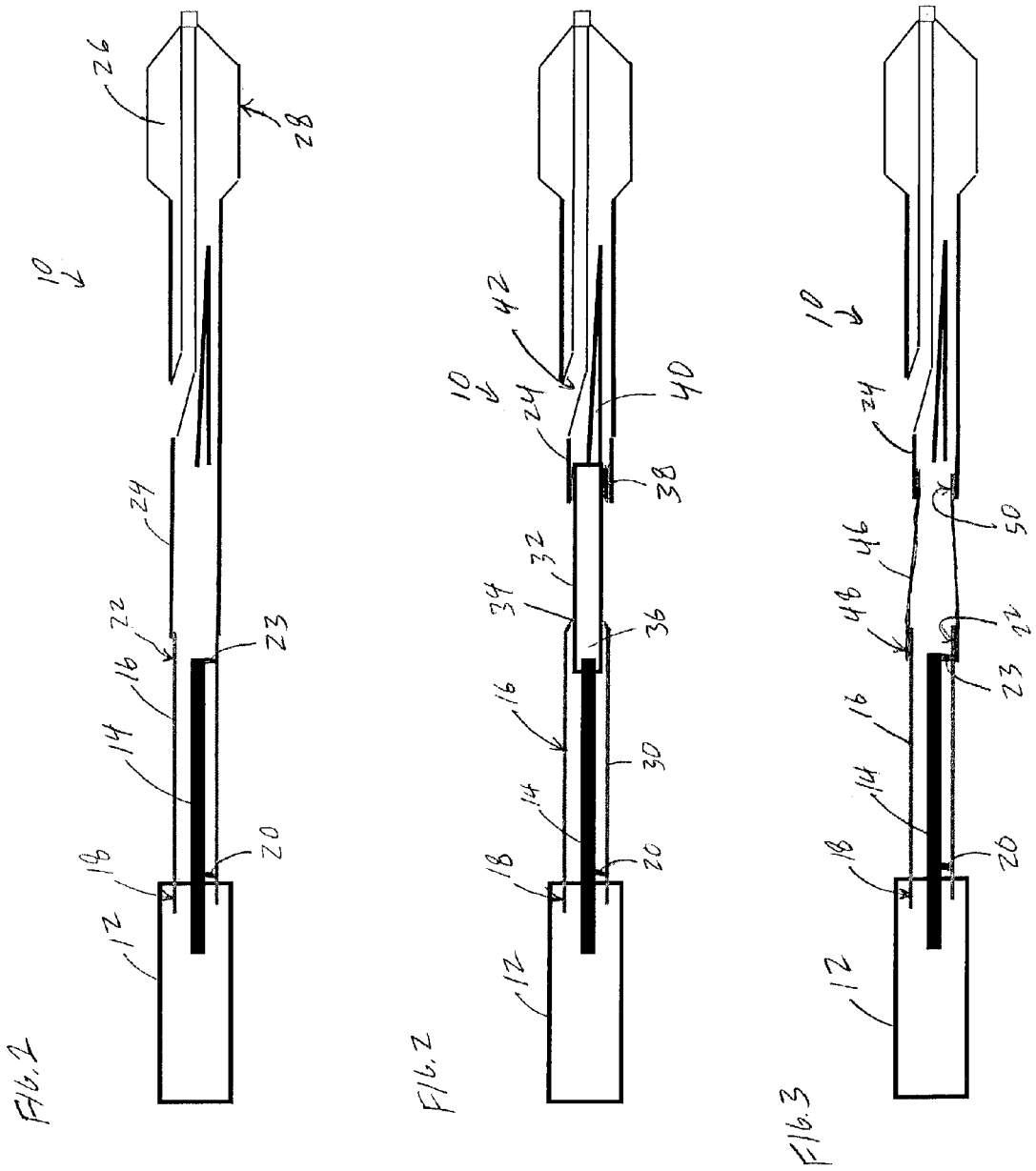

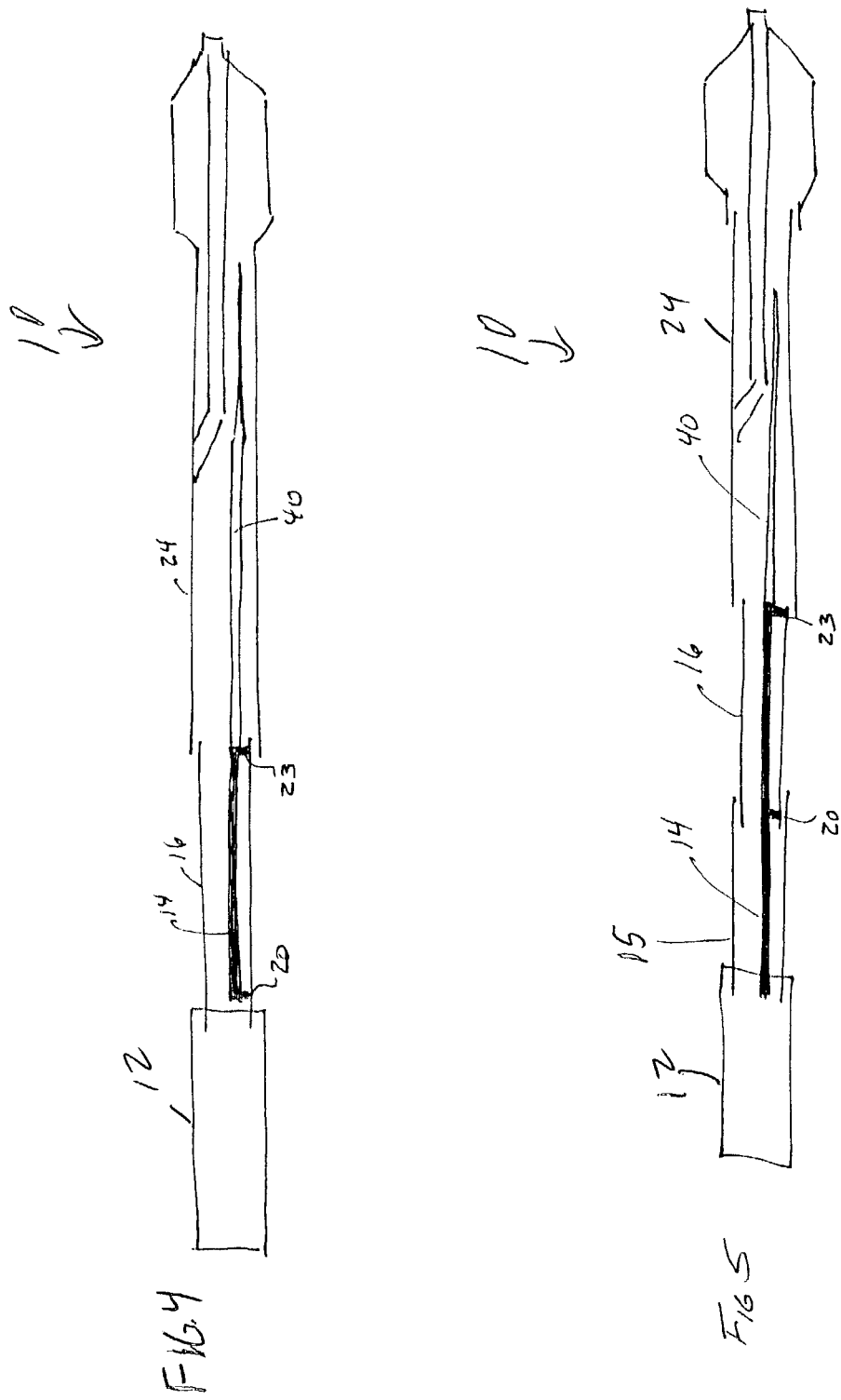

TETHER EQUIPPED CATHETER

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

The present invention is directed to a variety of embodiments. At least one embodiment of the invention is directed to the field of intravascular medical devices, and more particularly to the field of catheters such as angioplasty, neurological and guide catheters, among others, which may be used in various medical procedures such as percutaneous transluminal angioplasty (PTA), percutaneous transluminal coronary angioplasty (PTCA) as well as in procedures involving the placement of medicines and medical devices within the body.

Some embodiments of the invention are directed to all forms of catheters which may be advanced through a body lumen or vessel. Some examples of catheters are over-the-wire (OTW) catheters, such as are described in U.S. Pat. No. 5,047,045; single-operator-exchange (SOE) balloon catheters, such as are described in U.S. Pat. No. 5,156,594 and U.S. Pat. No. 5,549,552. Other examples of catheters which may incorporate the unique features of the present invention include monorail/rapid-exchange style balloon catheters, etc.

2. Description of the Related Art

Intravascular diseases are commonly treated by relatively non-invasive techniques such as PTA and PTCA. These angioplasty techniques typically involve the use of a balloon catheter. In these procedures, a balloon catheter is advanced through the vasculature of a patient such that the balloon is positioned proximate a restriction in a diseased vessel. The balloon is then inflated and the restriction in the vessel is opened. In other uses a catheter may be used to delivery an endoprosthesis such as a stent, graft, stent-graft, vena cava filter or other implantable device or devices herein after collectively referred to as a stent or stents. Where a stent is to be delivered into a body lumen the catheter may include one or more inflatable portions or balloons. Typically, the stent is retained in the predelivery state about the catheter shaft, or a portion thereof such as a balloon, by crimping and/or through the use of a retaining mechanism such as sleeve, sheath or sock.

Balloons and balloon catheters may be particularly useful for the delivery of expandable, implantable medical devices such as stents, grafts, stent-grafts, vena cava filters, hereinafter referred to cumulatively as stents. Stents and catheters used in their delivery are commonly used and as such their structure and function are well known.

Many catheters, including some types of balloon catheters, comprise a proximal portion referred to as a hypo-tube which is often constructed from a variety of non-thermoplastic and/or metallic material(s). The hypo-tube is often joined to a polymeric distal portion of the catheter at a port area by using a mid-shaft tube or by a distal extension of the hypo-tube itself. In some prior cases it is known that a catheter hypo-tube or a portion thereof may become structurally compromised while within a body vessel. Such structural compromise may lead to partial or complete fracture of the hypo-tube. When this occurs, the portion of the catheter proximal to the fracture may be withdrawn, but often times the distal portion of the catheter will continue to obstruct the vessel until it is surgically or otherwise removed from the vessel.

It is therefore a goal of the present invention is to provide a catheter assembly that includes a safety tether that is secured to one or more components of the catheter to ensure that all catheter components may be withdrawn from the body vessel even in the case of hypo-tube fracture.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

As indicated above, the present invention may be embodied in a variety of forms. In at least one embodiment the invention is directed to a catheter assembly which includes a wire, cord or other thin high tensile strength member that extends from the catheter manifold through the lumen of at least a portion of the catheter body. The wire is fixedly engaged in at least one point within the hypo-tube or proximal shaft of the catheter through which the wire passes. The wire acts as a tether allowing the portions of the catheter engaged to the wire, and/or portions proximal to the engagement point(s) to be withdrawn proximally even where the hypo-tube has fractured or otherwise failed.

In at least one embodiment the tether passes through at least a portion of the hypo-tube, the tether is engaged at the proximal end, distal end and/or other portions of the hypo-tube. In embodiments where the hypo-tube comprises two or more sections engaged together, such as for example where the proximal hypo-tube shaft is engaged to a hypo-tube mid-shaft, the tether may be engaged to the proximal end of the proximal portion and at least the proximal end of the hypo-tube mid-shaft.

In some embodiments, such as in a monorail or rapid exchange catheter and/or a catheter for use in balloon angioplasty and/or stent delivery, the catheter may be equipped with a distal core wire to provide transitional stiffness and support to the region of the catheter distal to the hypo-tube. In at least one embodiment the distal core wire is a continuation of the wire tether.

In some embodiments the tether is welded, bonded or otherwise engaged to selected areas of the hypo-tube and/or other catheter components.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

FIG. 1 is a cross-sectional longitudinal side view of an embodiment of the invention.

FIG. 2 is a cross-sectional longitudinal side view of an embodiment of the invention.

FIG. 3 is a cross-sectional longitudinal side view of an embodiment of the invention.

FIG. 4 is a cross-sectional longitudinal side view of an embodiment of the invention.

FIG. 5 is a cross-sectional longitudinal side view of an embodiment of the invention.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

As indicated above, FIG. 1 shows a longitudinal cross-section of a catheter assembly, indicated generally at 10. At its proximal end the catheter 10 comprises a manifold 12 from which a proximal core wire or tether 14 distally extends. In at least one embodiment the tether 14 is fixedly engaged to the manifold 12. However in some embodiments the tether may be engaged to any portion of the catheter assembly desired.

Catheter 10 includes a hypo-tube 16 that extends distally from manifold 12. The hypo-tube 16 is disposed about the portion of the tether 14 that extends distally from the manifold 12. A first end 18 of the hypo-tube 16 is engaged to the manifold 12 and/or a proximal engagement region 20 of the tether 14.

Tether 14 may comprise one or more wires, threads, cords, or other members that anchors at least a portion of the hypo-tube 16 to the manifold 12. Tether 14 preferably has a diameter that is as small as possible but which sufficiently large to provide an adequate safety tether that is unlikely to break in the event of the failure of the hypo-tube 16. In such a circumstance the tether has suitable strength to allow the retrieval of the portion of the catheter distal to the hypo-tube failure.

In at least one embodiment the diameter of the tether 14 is between 0.002 to about 0.015 inches in diameter. In at least one embodiment the tether is about 0.005 inches in diameter. In at least one embodiment the tether 14 is constructed of at least one metallic wire. The metallic wire may be stainless steel, nitinol, titanium, tantalum, Elgiloy, cobalt, chrome, nickel and any combinations or alloys thereof. In at least one embodiment the tether is at least partially constructed from a synthetic material such as for example Dacron® and/or Kevlar®, available from E. I. du Pont de Nemours and Company; carbon fiber; etc.

In the embodiment shown in FIG. 1, a portion of the hypo-tube 16, such as an end region 22, is engaged to the tether 14 at one or more engagement regions 23. The second end 22 is also engaged to a distal outer shaft 24. In some embodiments, an expandable medical device or balloon 26 is mounted on a portion of the distal outer shaft 24. At least a portion of the balloon 26 or a portion of the distal outer shaft 24 may define a stent mounting region 28 wherein a stent or other expandable medical device may be mounted for delivery by the catheter 10 into a body lumen or space.

In some embodiments the tether 14 extends through all or a substantial portion of the hypo-tube 16. The tether 14 may be engaged to more, and/or other, regions of the hypo-tube 16 other than the end regions 18 and 22 described above.

In some embodiments tether 14 may extend beyond the distal end 22 of the hypo-tube 16.

In the embodiment shown in FIG. 2 the hypo-tube 16 is comprised of a proximal portion 30 and a distal portion 32. Distal portion 32 is sometimes referred to as a mid-shaft portion. The proximal portion 30 is engaged to the distal portion 32 at a proximal shaft bond 34. The proximal shaft bond 34 defines a region of the portions 30 and 32 that are chemically bonded, chemically welded, heat welded or otherwise engaged together. The distal portion 32 of the hypo-tube 16 defines and end region 36. The tether 14 is engaged to at least a portion of the end region 36 of the distal portion 32 of the hypo-tube 16. If the proximal portion 30 of the hypo-tube 16 fractures or otherwise fails, the entire catheter may still be withdrawn from the body as the distal portion 32 remains anchored to the tether 14. In some embodiments the tether 14 is engaged to one or more other areas of the hypo-tube 16 in addition to or other than the end region 36.

The mid-shaft portion 32 extends distally to engage the distal outer shaft 24 at a mid-shaft engagement region 38. In some embodiments the distal outer shaft is at least partially constructed from one or more materials that are more flexible that mid-shaft portion 32. The mid-shaft engagement region 38 defines a region of the mid-shaft portion 32 and the distal outer shaft 24 that are chemically bonded, chemically welded, heat welded or otherwise engaged together. In some embodiments a distal core wire 40 extends distally from the mid-shaft portion 32 of the hypo-tube 16. The distal core wire 40 provides a transitional stiffness to the distal portion of the catheter 10 and provides internal support to the region of a catheter having a guide wire port 42 such as is shown. Because the tether 14 is engaged to mid-shaft 32, and the mid-shaft 32 is in turn engaged to the distal core wire 40, in some embodiments the mid-shaft 32 and core wire 40 function as an extension of the tether 14.

The distal core wire 40 extends distally and terminates distally of the mid-shaft engagement region 38. In at least one embodiment a portion of the wire 40 is fixed in positioned adjacent to the port 42. In some embodiments the wire 40 extends distally beyond the port 42.

In some embodiments, such as in the example shown in FIG. 3, the catheter 10 employs a mid-shaft tube 46 to act as a transitional connection between the hypo-tube 16 to the distal outer shaft 24. In at least one embodiment a first end 48 of the mid-shaft tube 46 is disposed about the end 22 of the hypo-tube 16. At least a portion of the distal outer shaft 24 is disposed about a second end 50 of the mid-shaft tube 46. Alternatively, the mid-shaft tube 46 may be engaged to hypo-tube 16 and/or the distal outer shaft 24 in any configuration known.

In the embodiment shown in FIG. 3 the tether 14 is engaged to at least one engagement area 23 of the hypo-tube 16 and/or the mid-shaft tube 46 as desired.

In some embodiments of the invention the tether 14 may be in continuous engagement with the hypo-tube 16.

In at least one embodiment, such as in the embodiment depicted in FIG. 4, the hypo-tube 16 extends from the manifold 12 directly to the distal outer shaft 24. In some embodiments the proximal engagement region 20 of the tether 14 is engaged to a portion of the hypo-tube 16 distal to the manifold 12. In such an embodiment the tether 14 may avoid being directly engaged to the manifold 12. The distal engagement region 23 of the tether 14 is at or adjacent to the second or distal end of the hypo-tube 16 and/or the distal outer shaft 24.

In some embodiments, an example of which is illustrated in FIG. 5, a shaft 15 of polymer material is positioned proximal of the hypo-tube 16 and distal of the manifold 12. A first end 17 of the polymer shaft 15 is engaged to the manifold 12. A second end 19 of the polymer shaft is engaged to at least a portion of the hypo-tube 16, including at least the first end 18. In at least this embodiment, the proximal engagement region 20 of the tether 14 is adjacent to or at the first end 18 of the hypo-tube 16 and/or the second end 19 of the polymer shaft 15. The distal engagement region 23 of the tether 14 is at or adjacent to the second or distal end of the hypo-tube 16 and/or the distal outer shaft 24. However, the tether 14 may be engaged to the polymer shaft 15, the hypo-tube 16 and/or the distal outer shaft 24 at any location or locations desired.

In some embodiments the distal core wire 40 extends from the tether 14 through at least a portion of the distal outer shaft 24.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A catheter assembly comprising:
   a manifold, the manifold being positioned at a proximal end of the catheter assembly;
   a tether member, the tether member having a proximal end region and a distal end region, at least a portion of the proximal end region being fixedly engaged directly to a portion of the manifold;
   a proximal tubular member, the proximal tubular member having a first end region and a second end region, at least a portion of the first end region being engaged to the manifold, the proximal tubular member being disposed about at least a portion of the tether member, at least a portion of the tether member distal of the manifold being fixedly engaged to at least a portion of the proximal tubular member.

2. The catheter assembly of claim 1 wherein at least a portion of the tether member is fixedly engaged to at least a portion of second end region of the proximal tubular member.

3. The catheter assembly of claim 1 wherein the tether member is comprised of at least one wire.

4. The catheter assembly of claim 3 wherein the at least one wire is at least partially constructed of at least one metal selected from the group consisting of: stainless steel, Elgiloy, nitinol, cobalt, chrome, titanium, nickel, tantalum and any combination thereof.

5. The catheter assembly of claim 1 wherein the tether member is at least partially constructed of at least one material of the group consisting of stainless steel, Elgiloy, nitinol, cobalt, chrome, titanium, tantalum, carbon fiber, Kevlar, Dacron and any combination thereof.

6. The catheter assembly of claim 1 wherein at least a portion of the tether member has a diameter of about 0.002 to about 0.015 inches.

7. The catheter assembly of claim 1 wherein at least a portion of the tether member has a diameter of about 0.005 inches.

8. The catheter assembly of claim 1 wherein at least a portion of the first end region of the proximal tubular member is engaged to a portion of the tether member.

9. The catheter assembly of claim 1 wherein the portion of the tether member distal of the manifold is in substantially continuous engagement with at least a portion of the proximal tubular member.

10. The catheter assembly of claim 1 wherein the proximal tubular member comprises a hypo-tube.

11. The catheter assembly of claim 10 wherein the hypo-tube is at least partially constructed of at least one metal.

12. The catheter assembly of claim 10 wherein the hypo-tube is at least partially constructed of at least one polymeric material.

13. The catheter assembly of claim 10 further comprising a mid-shaft member, at least a portion of the second end region of the hypo-tube being engaged to a portion of the mid-shaft member, at least a portion of the distal end region of the tether member being engaged to at least a portion of the mid-shaft member.

14. The catheter assembly of claim 13 wherein the mid-shaft member is more flexible than the hypo-tube.

15. The catheter assembly of claim 1 wherein the proximal tubular member comprises a first portion and a second portion, a distal end of the first portion being engaged to a proximal end of the second portion, the tether member being engaged to at least one region of each of the first portion and second portion.

16. The catheter assembly of claim 1 further comprising a distal outer tubular member, at least a portion of the second end region of the proximal tubular member being engaged to at least a portion of the distal outer tubular member.

17. The catheter assembly of claim 16 wherein the tether member is engaged to at least a portion of the distal outer tubular member.

18. The catheter assembly of claim 1 wherein a distal portion of the catheter defines a stent mounting region.

19. The catheter assembly of claim 1 further comprising a medical balloon, the medical balloon being mounted on a portion of a distal outer shaft, the distal outer shaft being engaged to the proximal tubular member.

20. The catheter assembly of claim 1 wherein the proximal tubular member defines a lumen, the tether member extending distally from the manifold and at least partially through the lumen of the proximal tubular member.

* * * * *